United States Patent
Hein, II et al.

(10) Patent No.: US 6,168,805 B1
(45) Date of Patent: Jan. 2, 2001

(54) AQUEOUS PROCESS FOR MANUFACTURING PAROXETINE SOLID DISPERSIONS

(75) Inventors: William A. Hein, II, Hasbrouck Heights, NJ (US); Sou-Chan Chang, Westbury; Huai-Hung D. Kao, Syosset, both of NY (US)

(73) Assignee: Endo Pharmaceuticals, Inc., Chadds Ford, PA (US)

( * ) Notice: Under 35 U.S.C. 154(b), the term of this patent shall be extended for 0 days.

(21) Appl. No.: 09/074,355

(22) Filed: May 7, 1998

(51) Int. Cl.[7] ............... A61K 9/14; A61K 9/20
(52) U.S. Cl. ............ 424/465; 424/464; 424/489; 514/770; 514/772.1; 514/772.3; 514/777; 514/781; 514/778; 514/782
(58) Field of Search .................. 424/464, 465, 424/451, 452, 489, 474

(56) References Cited

U.S. PATENT DOCUMENTS 5,597,826  1/1997  Howard et al. ............... 514/255

FOREIGN PATENT DOCUMENTS

| 0 810 224 A1 | 12/1997 | (EP) . |
| 95/16448 | 6/1995 | (WO) . |
| 98/31365 | 7/1998 | (WO) . |
| 99/00131 | 1/1999 | (WO) . |

Primary Examiner—James M. Spear
(74) Attorney, Agent, or Firm—Schrader Harrison Segal & Lewis LLP (57) ABSTRACT

A process for preparing solid, amorphous paroxetine comprising: (A) mixing paroxetine free base or a pharmaceutically acceptable paroxetine salt with water and pharmaceutically acceptable polymer; and (B) drying to form a composition comprising amorphous paroxetine and polymer, eliminating the need for organic solvents common for the solvent process. The resultant amorphous solid paroxetine composition is free from crystalline form, and yet has good handling properties, making it suitable for pharmaceutical use in the traditional tablet dosage form.

33 Claims, 12 Drawing Sheets

AQUEOUS PROCESS FOR MANUFACTURING PAROXETINE SOLID DISPERSIONS

BACKGROUND OF THE INVENTION

1. Field of the Invention

The present invention relates to processes for preparation of pharmaceutical compositions, the resultant compositions, and their use. Specifically, the present invention relates to pharmaceutical formulations of paroxetine, processes for the preparation of such formulations, pharmaceutical compositions containing the same and their use thereof in therapy.

2. Description of the Prior Art

The compound (−)-trans-4-((4'-fluorophenyl)3-(3'4'-methylenedioxyphenoxymethyl)-piperidine, commonly known as paroxetine, is a viscous oil and poorly water soluble drug which has been widely used pharmaceutical compositions, especially for depression.

U.S. Pat. No. 4,721,723 discloses crystalline paroxetine hydrochloride hemihydrate as a novel material with better handling properties than anhydrous paroxetine hydrochloride, a hygroscopic solid with poor handling properties.

Because U.S. Pat. No. 4,721,723 is based on the alleged better handling properties of crystalline paroxetine hydrochloride hemihydrate than anhydrous paroxetine hydrochloride, "a hygroscopic solid with poor handling properties" according to said U.S. patent, it has become an objective to provide anhydrous paroxetine which is not hygroscopic and has excellent handling properties and can be readily formulated into a commercial dosage form. Another object is to provide a process which eliminates the additional steps necesssary according to said U.S. patent to manufacture crystalline material, and thereby to reduce the manufacturing steps versus the steps required to produce the crystalline form.

International Patent Publication WO 96/24595 discloses paroxetine hydrochloride solvates other than the propan-2-ol solvate as precursors in the preparation of paroxetine hydrochloride substantially free of bound organic solvent. WO 96/24595 also discloses four novel paroxetine hydrochloride anhydrates substantially free of bound solvent.

International Patent Application WO 97/03670 published Feb. 6, 1997 discloses controlled release paroxetine formulation comprising "a reaction complex formed by the interaction of (1) a calcium polycarbophil component which is a water-swellable, but water insoluble, fibrous cross-linked carboxy-functional polymer, said polymer containing (a) a plurality of repeating units of which at least about 80% contain at least one carboxyl functionality, and (b) about 0.05 to about 1.5% cross-linking agent substantially free from polyalkenyl polyether, said percentages being based upon the weights of unpolymerized repeating unit and cross-linking agent, respectively, with (2) water, in the presence of an active agent selected from the group consisting of SSRI's such as paroxetine . . . a further particular aspect [of the WO 97/03670 invention] provides a system for the controlled release of an active substance which is an SSRI such as paroxetine, comprising (a) a deposit-core comprising an effective amount of the active substance having defined geometric form, and (b) a support-platform applied to said deposit-core, wherein said deposit-core contains at least the active substance, and at least one member selected from the group consisting of (1) a polymeric member which swells on contact with water or aqueous liquids and a gellable polymeric material . . . and (2) a single polymeric material having both swelling and gelling properties, and wherein the support platform is an elastic support, applied to said deposit-core so that it partially covers the surface of the deposit-core and is slowly soluble and/or slowly gellage in aqueous fluids. The support-platform may comprise polymers such as hydroxypropylimethylcellulose, plasticizers such as glyceride, binders such as polyvinylpyrrolidone, hydrophillic agents such as lactose and silica, and/or hydrophobic agents such as magnesium stearate and glycerides . . . Preferably the paroxetine is suitably in the form of the [crystalline] hydrochloride hemihydrate [which may be] prepared according to the procedures generally outlined in U.S. Pat. No. 4,721,723."

There has been a need in the art to provide novel processes for incorporating paroxetine, a poorly water soluble drug, into a solid dispersion and its use in pharmaceutical compositions containing the same.

SUMMARY OF THE INVENTION

These objects, and others which will become apparent from the following disclosure, are achieved by the present invention which, in one aspect, comprises a process for preparing solid, amorphous paroxetine comprising:

(A) mixing paroxetine free base or a pharmaceutically acceptable paroxetine salt with water and pharmaceutically acceptable polymer; and (B) drying to form a composition comprising amorphous paroxetine and polymer.

In another aspect, the invention comprises a pharmaceutical composition comprising paroxetine salt in amorphous, solid form, and polymer, prepared by the aforementioned process.

A still further aspect of the invention is a process of treating a warm-blooded animal comprising administering the pharmaceutical composition prepared according to this invention.

The aqueous solvent process of the invention eliminates the need for organic solvents and provides an amorphous solid form having distinct advantages over the crystalline form of the prior art.

DETAILED DESCRIPTION OF THE INVENTION AND THE PREFERRED EMBODIMENTS

Paroxetine is the generic name for the compound described in Example 2 of U.S. Pat. No. 4,007,196, also known as (−)-trans-4-(4'-fluorophenyl)- 3-(3',4'-ethylenedioxyphenoxymethyl)-piperidine, and pharmaceutically acceptable salts thereof. Paroxetine free base is a viscous oil at standard temperature and pressure. The paroxetine salts are acid addition products of paroxetine. For example, the hydrogen chloride acid addition product is called "paroxetine hydrochloride" or "paroxetine hydrochloride salt."

The compound paroxetine herein described has two asymmetric centers. Unless otherwise indicated, the (−)-trans isomer is the preferred enantiomer. However, all chiral, diastereomeric and racemic forms can be used. It is well known in the art how to prepare optically active forms, such as by resolution of racemic forms or by synthesis, from optically active starting materials. Use of all chiral, diastereomeric, racemic forms are intended, unless the specific stereochemistry or isomer form is specifically indicated.

The pharmaceutically acceptable polymeric carriers used in the invention can be, for example, hydroxypropyl cellulose, methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polypropylene, dextrans, dextrins, hydroxypropyl-beta-cyclodextrin, chitosan, co(lactic/glycolid) copolymers, poly(orthoester), poly(anhydrate), polyvinyl chloride, polyvinyl acetate, ethylene vinyl acetate, lectins, carbopols, silicon elastomers, polyacrylic polymers, maltodextrins, lactose, fructose, inositol, trehalose, maltose, raffinose, polyvinylpyrrolidone (PVP), polyethylene glycol (PEG), and alpha-, beta-, and gamma-cyclodextrins, or suitable mixtures of thereof.

Preferred polymeric carriers are one or more of polyvinylpyrrolidone, hydroxypropylmethyl cellulose, hydroxypropyl cellulose, methyl cellulose, block co-polymers of ethylene oxide and propylene oxide, and polyethylene glycol, wherein a more preferred polymeric carrier is polyvinylpyrrolidone (PVP) having an average molecular weight of from about 2,500 to about 3,000,000. A most preferred polymeric carrier is polyvinylpyrrolidone having an average molecular weight of from about 10,000 to about 450,000. It is preferred that the polymer is not of a character which controls or delays the release of said paroxetine from a solid tablet formulation since immediate release formulations have been found to be the most preferable.

The pharmaceutically acceptable carrier is preferably miscible with both the paroxetine free base and the salt, capable of keeping the salt in a homogeneous noncrystalline solid state dispersion after the water has been removed by evaporation and chemically inert with respect to the free base of the active ingredient, the salt of the free base, and the aqueous acid solution. The polymer is preferably at least partially water soluble, and more preferably is fully water soluble.

Suitable pharmaceutically acceptable salts include, but are not limited to, mineral or organic acid salts, quaternary ammonium salts, and the like. Examples of pharmaceutically acceptable salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethanesulfonic, ethanedisulfonic, oxalic, isothyanic, and the like.

The pharmaceutically acceptable salts of paroxetine can be prepared by introduction of or delivery of the acid moiety by various means. The acidic moiety could be introduced in neat form or as an aqueous solution. Generally, the salts are prepared by reacting the free base with stoichiometric amounts or with an excess of the desired salt-forming inorganic or organic acid.

Lists of suitable salts are found in Remington's Pharmaceutical Sciences, 17th ed., Mack Publishing Company, Easton, Pa., 1985, p. 1418, the disclosure of which is hereby incorporated by reference.

The paroxetine may be added in either free base or salt form. When the paroxetine is added in free base form, the process comprises adding an acid corresponding to a pharmaceutically acceptable salt of paroxetine to the mixture or solution of the free base. The free base is then converted to a salt in situ, for example by addition of an inorganic or an organic acid. The acid is added either as a gas, a liquid or as a solid dissolved into water. The preferred acid is hydrogen chloride and the molar quantity of acid added to the solution of paroxetine free base and carrier may either be in stoichiometric proportion to the paroxetine free base or be in excess of the molar quantity of the paroxetine free base, especially when added as a gas.

The preferred range of hydrogen chloride added is about 1.0 to about 1.8 times the molar quantity of paroxetine free base. Preferred molar ratios of paroxetine to HCl are about 1:1 to 1:1.8, more preferably about 1:1.1. Although hydrogen chloride is readily added as a gas, the preferred method to add the hydrogen chloride is in the form of hydrogen chloride dissolved into water. It is understood that upon addition of the acid, the formed free base salt remains dissolved in solution with the polymeric carrier.

The paroxetine, polymeric carrier, and water may be combined in any order. It is preferred that they be combined in a manner so as to form a solution of paroxetine salt and the polymer.

In forming a solution of polymeric carrier and water, heating of the solution is not necessary at lower concentrations but is strongly preferred at higher concentrations, provided that the temperature does not result in decomposition or degradation of any materials. It is preferred to add the paroxetine free base or paroxetine salt after dissolving the polymer in water, suitably at 25 to 100° C., preferably at 45 to 80° C. When the paroxetine is added as a free base, it is preferred to form a salt at a temperature at which the final solution is clear. For the most preferred embodiments, a temperature of at least about 60° C. results in a clear solution of the paroxetine salt being formed, although for other concentrations and embodiments, clear solutions are formed at other temperatures. It is preferred to only add enough heat to form a clear solution.

The ratio by weight of water soluble pharmaceutically acceptable polymeric carrier to paroxetine salt is in the range of about 20:1 to about 0.5:1; preferably about 4:1 to about 1:1; more preferably about 3:1 to about 1.5:1; most preferably about 2:1.

Preferably a clear solution is formed. Upon formation of the preferred clear solution, the process proceeds by recovering the water to form a solid state dispersion of the free base salt in the polymeric carrier. Any method of removal of the water which renders a homogeneous solid state dispersion is intended, although preferred are methods of evaporation under vacuum or spray drying. Preferred methods of evaporation under vacuum include rotoevaporation, static vacuum drying and the combination thereof. It is understood that one skilled in the art of pharmaceutical formulations can determine a reasonable temperature at which water can be removed, provided the temperature is not so high as to cause degradation or decomposition of the materials; however, it is preferred that evaporation occurs at about 25° C. to about 100° C. It is also preferred that evaporation of water renders a solid state dispersion which is homogeneous and substantially free of water. By substantially free it is meant that the solid state dispersion contains less than 20% by weight of residual water, preferably less than 10%, more preferably less than 5%, most preferably less than 1%.

In addition to the amorphous paroxetine salt, other active ingredients can be added, preferably in water-soluble salt form, so as to form combinations of more than one drug in amorphous form. In view of the preference for immediate release formulations, it is very much preferred that the solid formulation be free of calcium polycarbophil, which is used in the prior art as a controlled release agent. In fact it is preferred that the composition be free of any water-swellable, insoluble, fibrous cross-linked carboxy-functional polymer, which were used in the prior art for controlled release.

The ratio of paroxetine to the pharmaceutically acceptable polymeric carrier can be varied over a wide range and depends on the concentration of paroxetine required in the pharmaceutical dosage form ultimately administered.

The ratio of paroxetine free base to the pharmaceutically acceptable carrier can be varied over a wide range and depends on the concentration of paroxetine required in the pharmaceutical dosage form ultimately administered. However, the preferred range of paroxetine in the solid dispersion is about 16% to about 50% of the total solid dispersion weight, more preferable is about 20% to about 50%, even more preferable is about 25% to about 40%, most preferable is about 33% of the total dispersion weight. In terms of weight ratio of polymer to paroxetine, a preferred range is about 0.4:1 to 20:1.

Suitable pharmaceutically acceptable excipients can be added in the process. Suitable pharmaceutical excipients are described in Remington's Pharmaceutical Sciences, Mack Publishing Company, a standard reference text in this field.

Examples of pharmaceutically acceptable excipients include diluents, binders, disintegrants, coloring agents, flavoring agents, lubricants and/or preservatives. The pharmaceutical composition may be formulated by conventional methods of admixture such as blending, filling, granulation and compressing. These agents may be utilized in conventional manner, for example in a manner similar to that already used clinically for anti-depressant agents.

The composition is usually presented as a unit dose composition containing from 1 to 200 mg, more usually from 5 to 100 mg, for example 10 to 50 mg such as 12.5, 20, 25, or 30 mg. Such composition is normally taken from 1 to 6 times daily, for example 2, 3, or 4 times daily so that the total amount of active agent administered is within the range of 5 to 400 mg.

Preferred unit dosage forms include tablets or capsules.

The invention also provides for a method of treatment of depression in mammals including humans which method comprises administering an effective amount of pharmaceutically acceptable solid state dispersion of paroxetine hydrochloride.

The invention further provides a formulation of paroxetine hydrochloride for use in the treatment of depression.

The method of this invention can be administered by any means that produces contact of the active agent with the agent's site of action, serotonin re-uptake inhibition, in the body of a mammal. They can be administered by any conventional means available for use in conjunction with pharmaceuticals, either as individual therapeutic agents or in a combination of therapeutic agents.

The dosage of the novel compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–50% by weight based on the total weight of the composition.

The active ingredient can be administered orally in solid dosage forms, such as capsules, tablets, and powders.

Gelatin capsules contain the active ingredient and excipients, such as lactose, starch, cellulose derivatives, magnesium stearate, stearic acid, and the like. Similar excipients can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

A few examples of pharmaceutical dosage-forms for administration of the compounds of this invention are illustrated as follows:

Unit capsules can be prepared by filling standard two-piece hard gelatin capsules each with 10 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil can be prepared and injected by means of a positive displacement pump into gelatin to form soft gelatin capsules containing 10 milligrams of the active ingredient. The capsules would then be washed and dried.

Tablets can be prepared by conventional procedures, for example in the dosage units of 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The active ingredient may be administered with pharmaceutically acceptable excipients. The pharmaceutically acceptable excipients include calcium carbonate, calcium phosphate, calcium sulfate, cellulose, cellulose derivatives, croscarmallose sodium, cospovidone, dextrates, dextrin, dextrose, fructose, guar gum, lactose, maltodextrin, mannitol, povidone, starch, sorbitol, sucrose, xylitol and mixtures thereof. Pharmaceutically acceptable cellulose derivatives include hydroxypropyl celluose, methyl cellulose, carboxymethyl cellulose, sodium carboxymethyl cellulose, cellulose acetate phthalate, cellulose acetate butyrate, hydroxyethyl cellulose, ethyl cellulose and the like. The active ingredient may be mixed with pharmaceutically acceptable excipient and tabletized.

The following examples further illustrate specific embodiments of the present invention, and are to be considered an illustrative, but not limiting. Examples 1–5, show the preparation of solid state dispersions while Examples 6 and 7 show pharmaceutical compositions.

EXAMPLES

Example 1
PVP 29/32K/PAROXETINE HYDROCHLORIDE, 2:1 WT BASIS, OVEN DRYING

Figure 1:
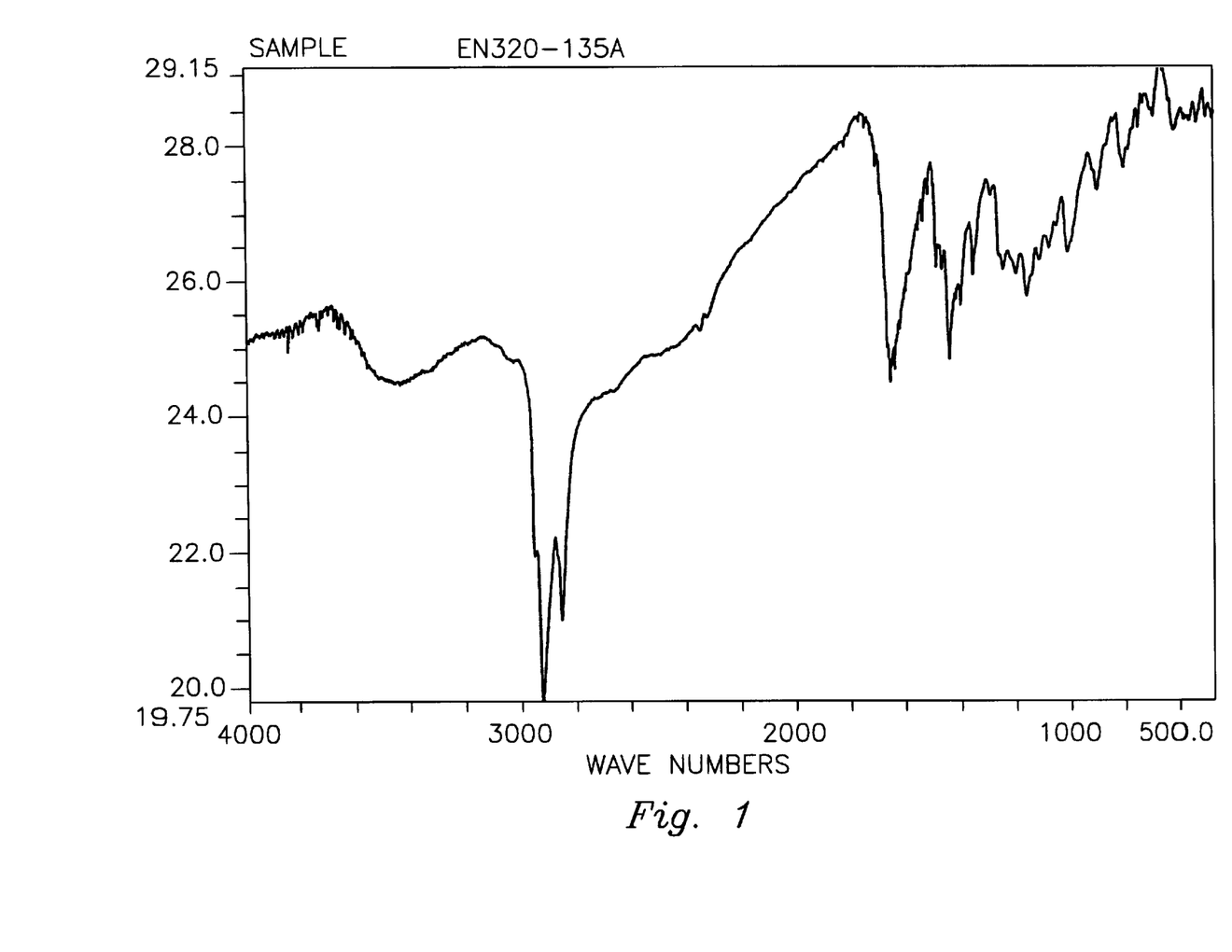
FIG. 1 is an FTIR analysis of Sample No. EN320-135A.
Figure 2:
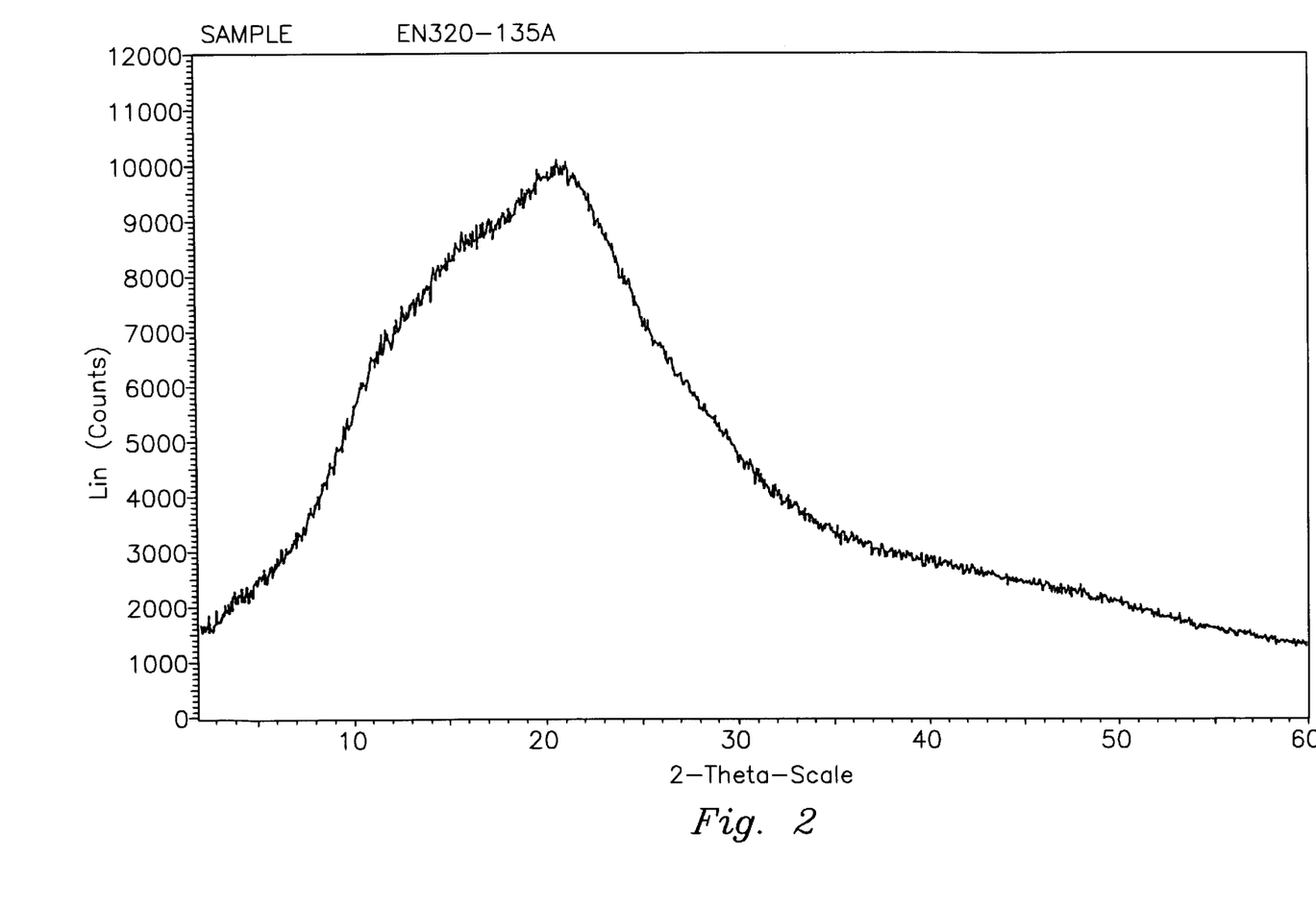
FIG. 2 is an x-ray powder defraction analysis of Sample No. EN320-135A.

To a 125 mL Erlenmeyer flask was added PVP 29/32K (8.1210 g), paroxetine free base (4.62 g) and hot purified water (60° C., 48 mL). The Erlenmeyer flask was immersed in water bath heated to 60° C. Hot 1.0 N HCl (60° C., 13.6 mL) was added to the 125 mL Erlenmeyer flask and stirred for approximately 5 minutes. Approximately 5 mL of the hot solution was transferred using a pipette to a pre-heated crystallization dish (60° C.) and dried in a tray oven at 60° C. for 71 hours. The solid product, identified as EN320-135A, was tested by FTIR (FIG. 1) and x-ray powder diffraction (FIG. 2). FTIR analysis results were wholly consistent with PVP and paroxetine hydrochloride. No crystalline peaks were found in the x-ray powder diffraction indicating absence of crystalline paroxetine and that paroxetine was present in amorphous form only. The FTIR data was collected using a Nicolet 510P FT-IR spectrometer. A Nujol mull was prepared for the sample and analyzed on a KBr plate. The x-ray powder patterns were obtained using a Bruker Analytical GADDS system. The diffractometer was equipped with a point x-ray source and a 2-dimensional area detector. The radiation was CuK (alpha, 50 kV, 40 mA). The data were collected at room temperature from 2 to 60 degrees 2-theta; the detector range was 30 degrees; the number of frames was 3; the data collection time was 600 sec/frame. The sample was mounted for reflection mode data collection by pressing the sample into a small round sample holder.

$^1$H NMR analysis (CDCl$_3$) were wholly consistent with a mixture of PVP and paroxetine hydrochloride, and showed the expected resonances for PVP (series of br. m 3.8–1.6) and the characteristic signal for paroxetine hydrochloride (2.9, br. dt).

Elemental Analysis: Calcd. for 8.121: 5.13 (wt. basis) PVP and paroxetine HCl: % C, 62.33; % H, 7.34; % N, 8.72; % Cl, 3.62; % F, 1.94. Found: % C, 60.72; % H, 7.28; % N, 8.67; % Cl, 3.87; % F, 2.07.

Example 2
PVP 29/32K/PAROXETINE HYDROCHLORIDE, 2:1 WT BASIS, VACUUM DRYING

Figure 3:
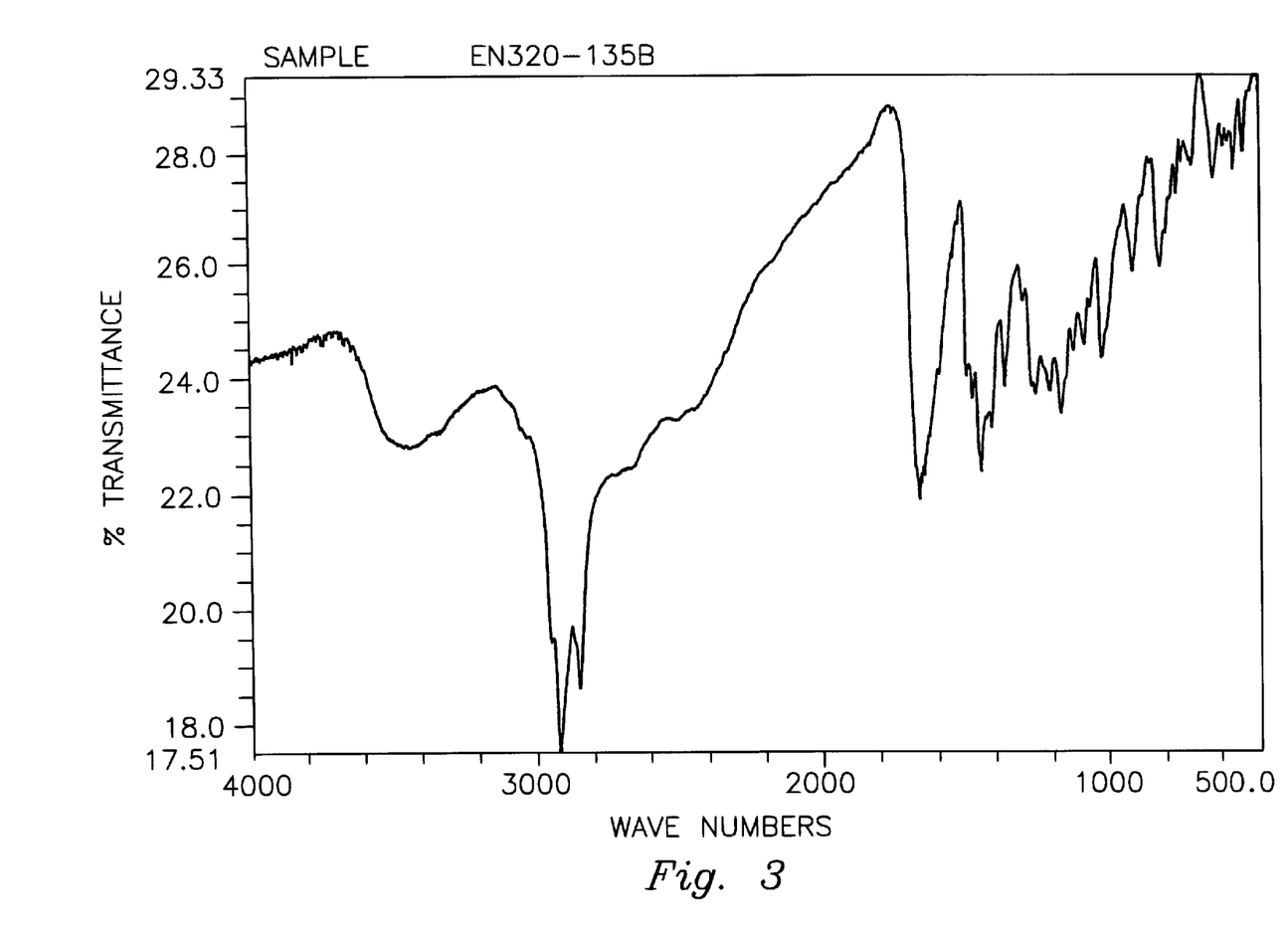
FIG. 3 is an FTIR analysis of Sample No. EN320-135B.
Figure 4:
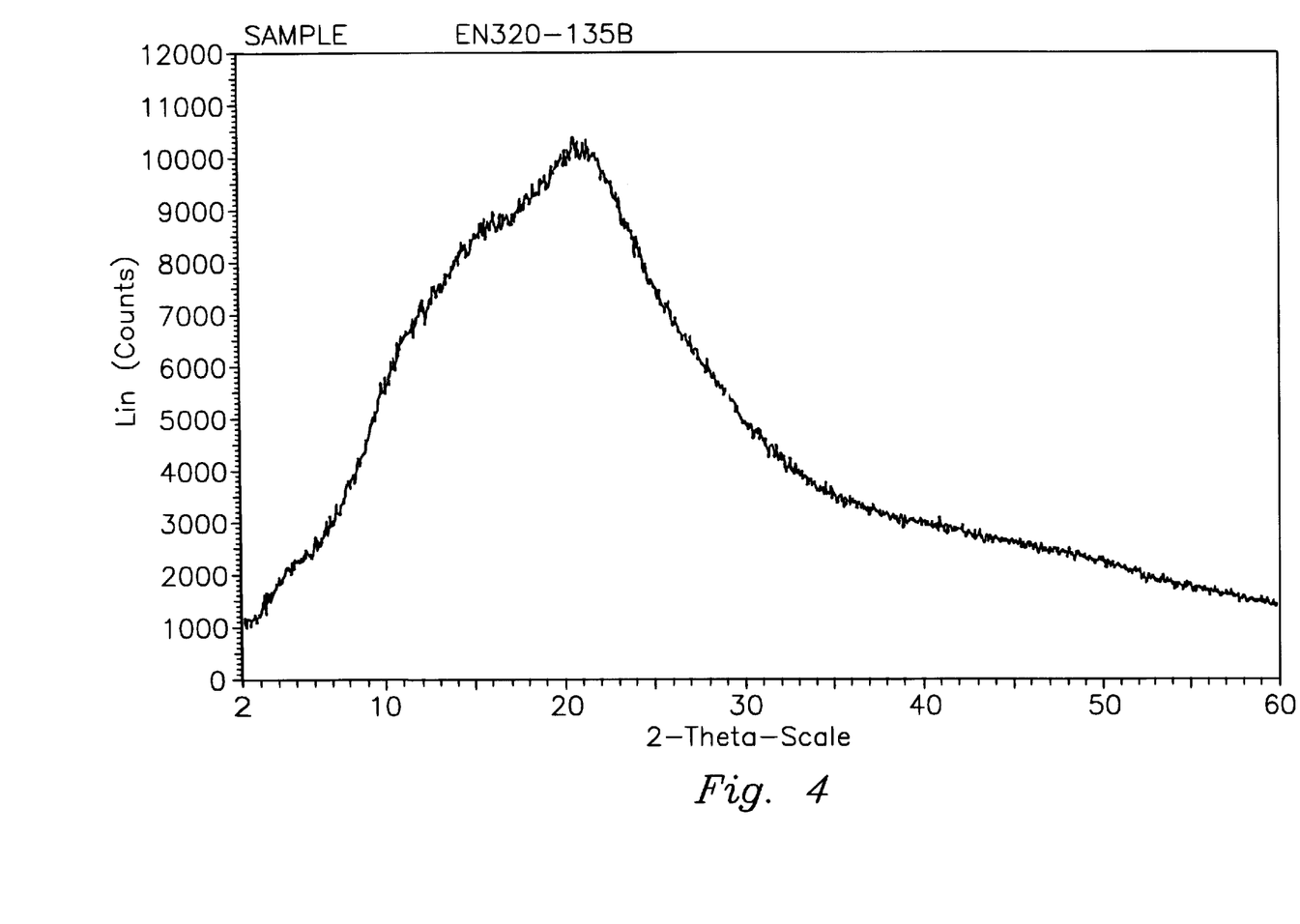
FIG. 4 is an x-ray powder defraction analysis of Sample No. EN320-135B.

Approximately 5 mL of the hot solution prepared in Example 1 was transferred using a pipette to a pre-heated 50 mL round bottom flask (60° C.). The sample was dried under static vacuum at 60° C. for 29 hours. The solid product, identified as EN320-135B, was tested by FTIR (FIG. 3) and x-ray powder diffraction (FIG. 4). FTIR analysis results were wholly consistent with PVP and paroxetine hydrochloride. No crystalline peaks were found in the x-ray powder diffraction indicating absence of crystalline paroxetine and that paroxetine was present in amorphous form only. The FTIR data was collected using a Nicolet 510P FT-IR spectrometer. A Nujol mull was prepared for the sample and analyzed on a KBr plate. The x-ray powder patterns were obtained using a Bruker Analytical GADDS system. The diffractometer was equipped with a point x-ray source and a 2-dimensional area detector. The radiation was CuK (alpha, 50 kV, 40 mA). The data were collected at room temperature from 2 to 60 degrees 2-theta; the detector range was 30 degrees; the number of frames was 3; the data collection time was 600 sec/frame. The sample was mounted for reflection mode data collection by pressing the sample into a small round sample holder.

$^1$H NMR analysis (CDCl$_3$) were wholly consistent with a mixture of PVP and paroxetine hydrochloride, and shows the expected resonances for PVP (series of br. m 3.8–1.6) and the characteristic signal for paroxetinea hydrochloride (2.9, br. dt).

Elemental Analysis: Calcd. for 8.121: 5.13 (wt. basis) PVP and paroxetine HCl: % C, 62.33; % H, 7.34; % N, 8.72; % Cl, 3.62; % F, 1.94. Found: % C, 61.49; % H, 7.30; % N, 8.84; % Cl, 3.89; % F, 2.03.

Figure 5:
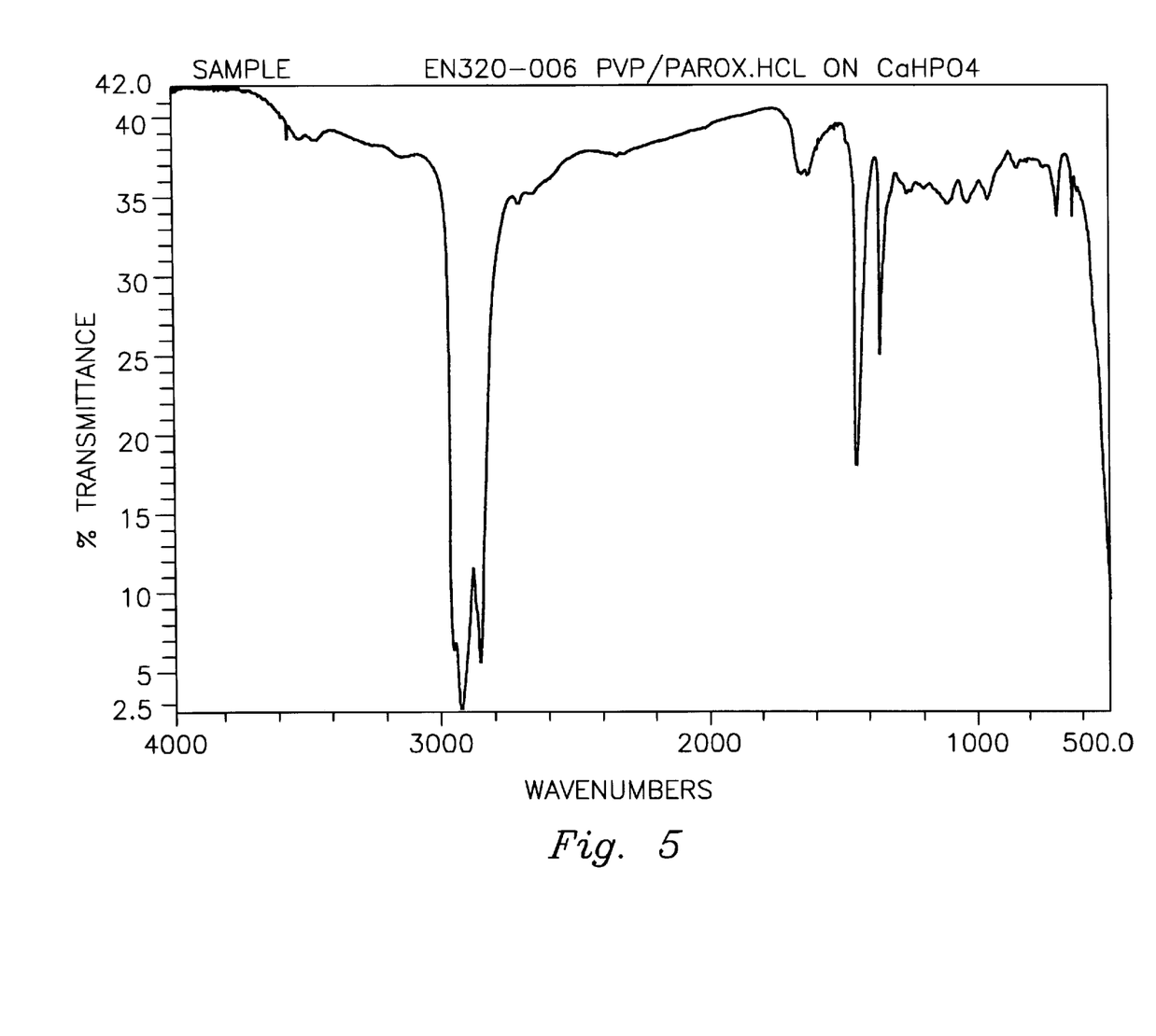
FIG. 5 is an FTIR analysis of Sample No. EN320-006.
Figure 6:
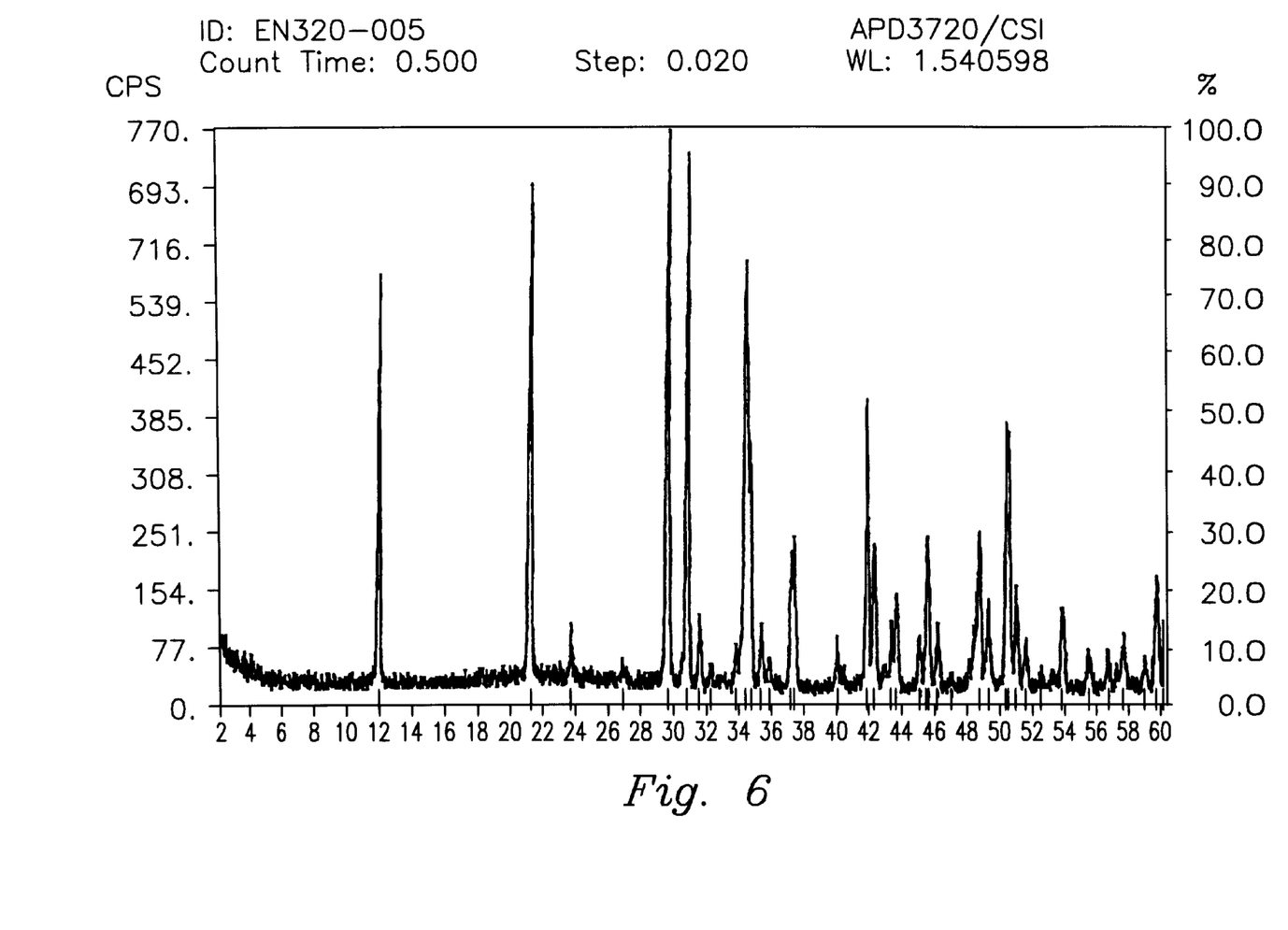
FIG. 6 is an x-ray powder defraction analysis of Sample No. EN320-006.

Example 3
PVP 29/32K/PAROXETINE HYDROCHLORIDE, 2:1 WT BASIS, FLUID BED DRYING:

To a 250 mL flask (equipped with a magnetic stir bar) was added polyvinylpyrrolidone (PVP) having a molecular weight distribution corresponding to 29/32K (14.0097 g), paroxetine hydrochloride anhydrous isopropyl alcohol solvate (7.0058 g) and purified water (85.366 g). The contents of the flask were stirred and heated to a temperature of approximately 60° C. with a stirring hotplate to obtain a clear solution. The hot solution was spray dried onto dibasic calcium phosphate dihydrate (100.0 g) using a bench top fluid bed dryer. FTIR (FIG. 5) analysis of the solid, free-flowing powder, identified as EN320-006, was consistent with a mixture of dibasic calcium phosphate dihydrate, PVP and paroxetine hydrochloride. X-ray powder diffraction (FIG. 6) analysis of the powder was wholly consistent with a mixture of dibasic calcium phosphate dihydrate and PVP, indicating absence of crystalline paroxetine and that the paroxetine was present in amorphous form only. The FTIR data was collected using a Nicolet 510P FT-IR spectrometer. A Nujol mull was prepared for the sample and analyzed on a KBr plate. The x-ray powder patterns were obtained using a Philips model 3720 automated powder diffractometer. The diffractometer was equipped with a varaible slit (theta-compensating slit), a scintillation counter, and a graphite monochromater. The radiation was CuK (alpha, 40 kV, 30 mA). The data were collected at room temperature from 2 to 60 degrees 2-theta; the step size was 0.02 degrees; the count time was 0.5 sec/step. The sample was prepared on a glass specimen holder as a thin layer of powdered material in a dry neat state.

Figure 7:
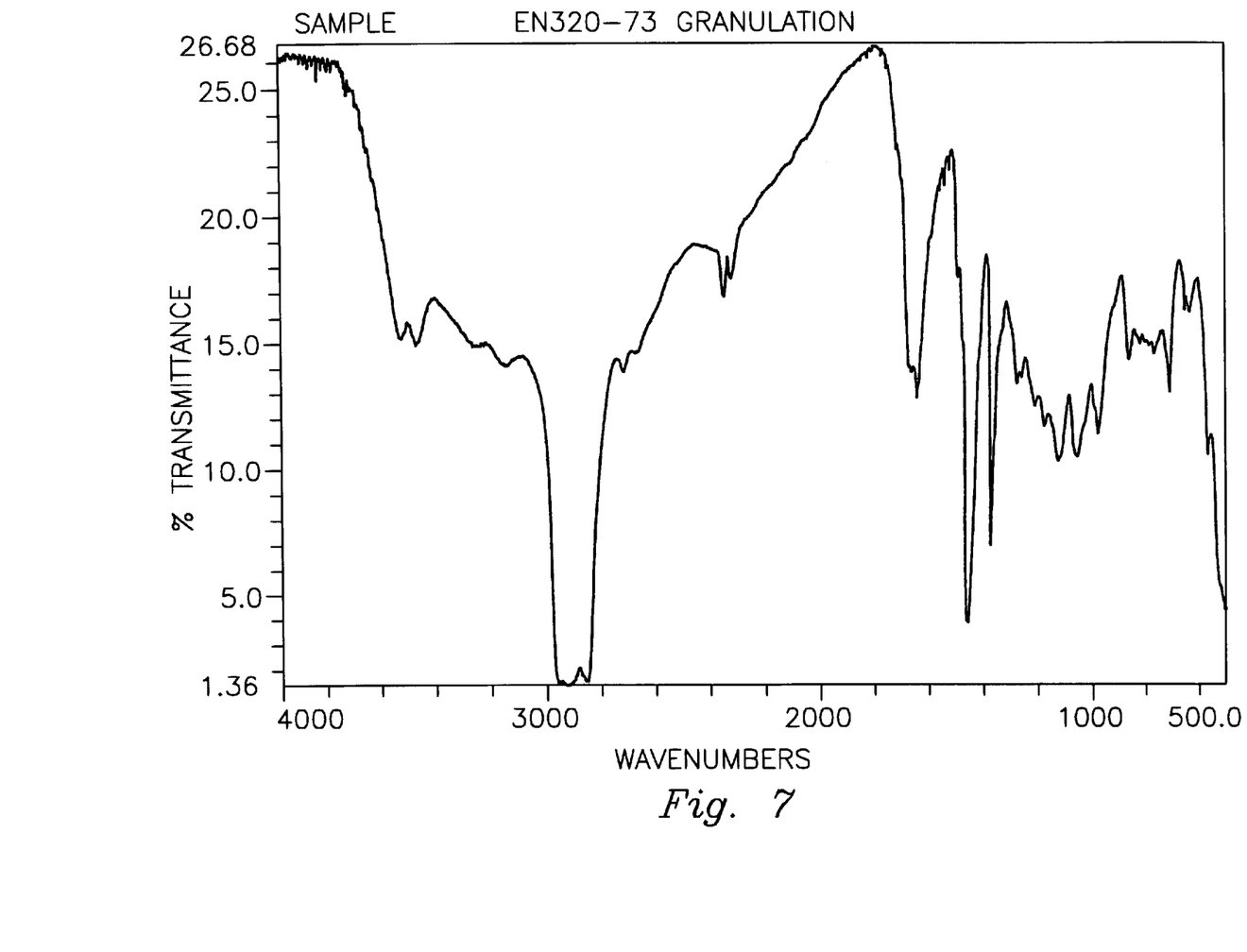
FIG. 7 is an analysis of Sample No. EN320-073.
Figure 8:
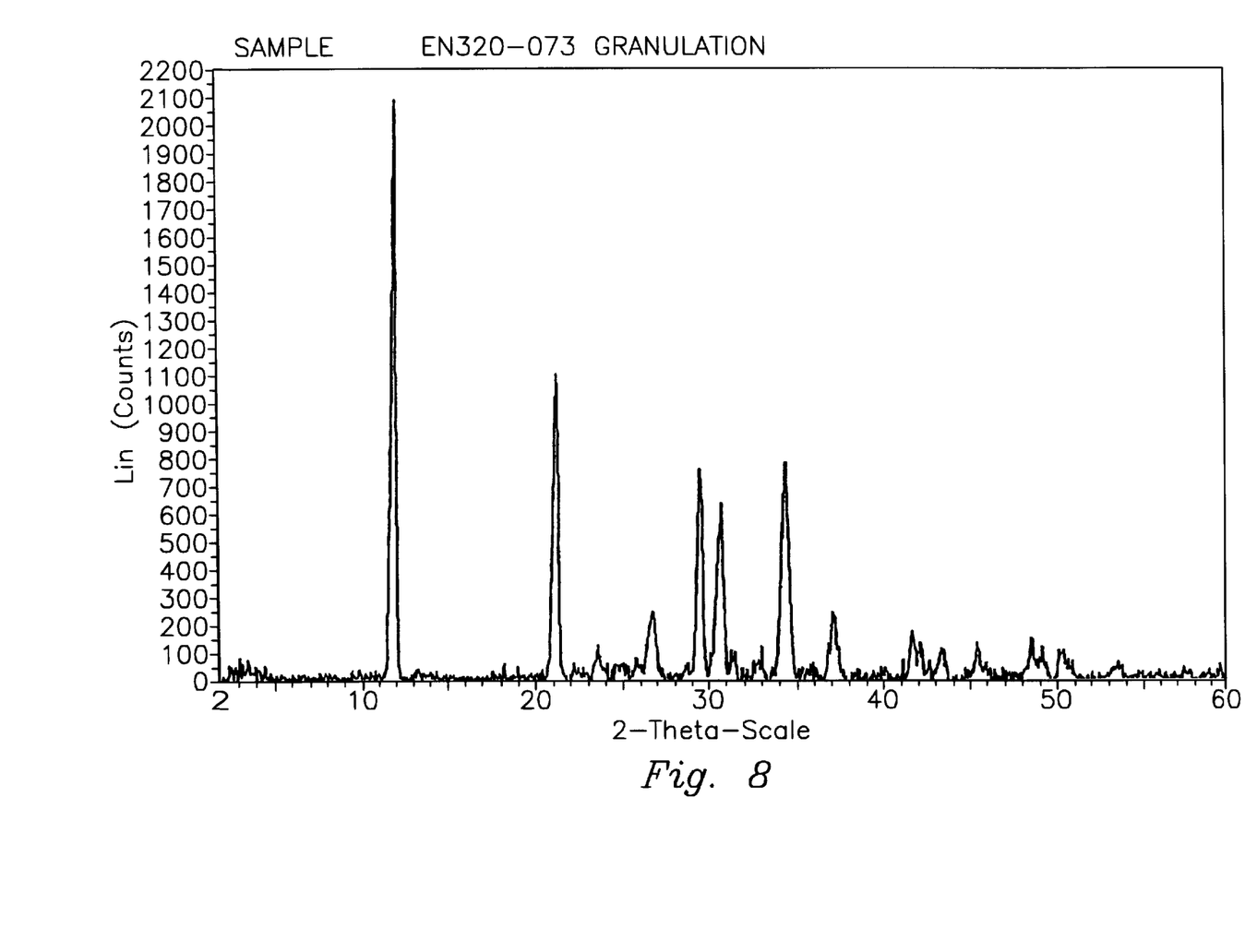
FIG. 8 is an x-ray powder defraction analysis of Sample No. EN320-073.

Example 4
PVP 29/32K/PAROXETINE HYDROCHLORIDE, 1:1 WT BASIS, FLUID BED DRYING To a 250 mL flask (equipped with a magnetic stir bar) was added PVP 29/32K (22.24 g), paroxetine hydrochloride anhydrous isopropyl alcohol solvate (22.21 g) and purified water (278 g). The contents of the flask were stirred and heated to a temperature of approximately 60° C. with a stirring hotplate to obtain a clear solution. The hot solution was spray dried onto dibasic calcium phosphate dihydrate (187.344 g) using a bench top fluid bed dryer. FTIR (FIG. 7) analysis of the solid, free-flowing powder, identified as EN320-073, was consistent with a mixture of dibasic calcium phosphate dihydrate, PVP and paroxetine hydrochloride. X-ray powder diffraction (FIG. 8) analysis of the powder was wholly consistent with a mixture of dibasic calcium phosphate dihydrate and PVP, indicating absence of crystalline paroxetine and that the paroxetine was present in amorphous form only. The FTIR data was collected using a Nicolet 510P FT-IR spectrometer. A Nujol mull was prepared for the sample and analyzed on a KBr plate. The x-ray powder patterns were obtained using a Bruker Analytical GADDS system. The diffractometer was equipped with a point x-ray source and a 2-dimensional area detector. The radiation was CuK (alpha, 50 kV, 40 mA). The data were collected at room temperature from 2 to 60 degrees 2-theta; the detector range was 30 degrees; the number of frames was 3; the data collection time was 600 sec/frame. The sample was mounted for reflection mode data collection by pressing the sample into a small round sample holder.

Example 5
PVP 29/32K/PAROXETINE HYDROCHLORIDE, 0.5:1 WT BASIS, FLUID BED DRYING

Figure 9:
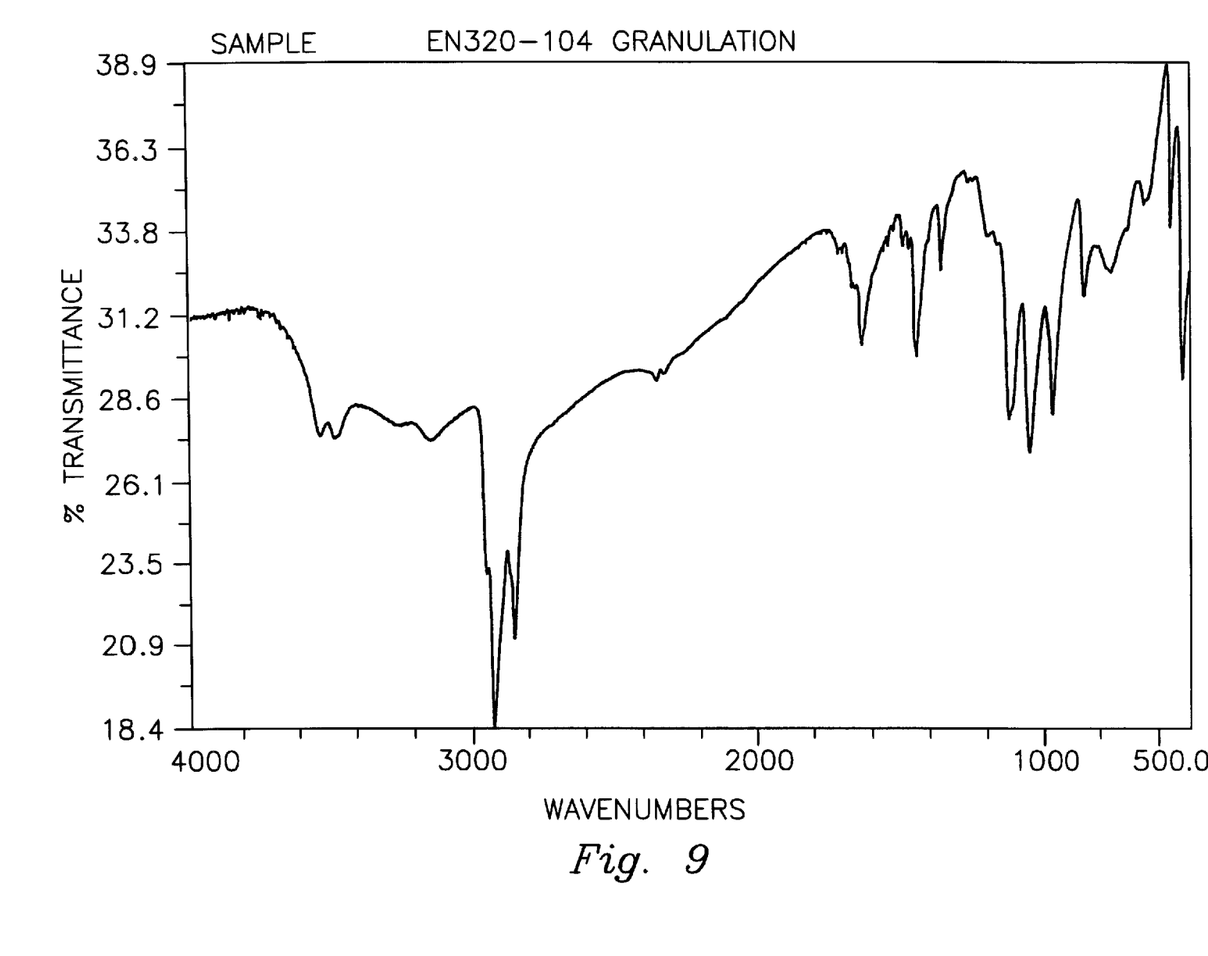
FIG. 9 is an FTIR analysis of Sample No. EN320-104.
Figure 10:
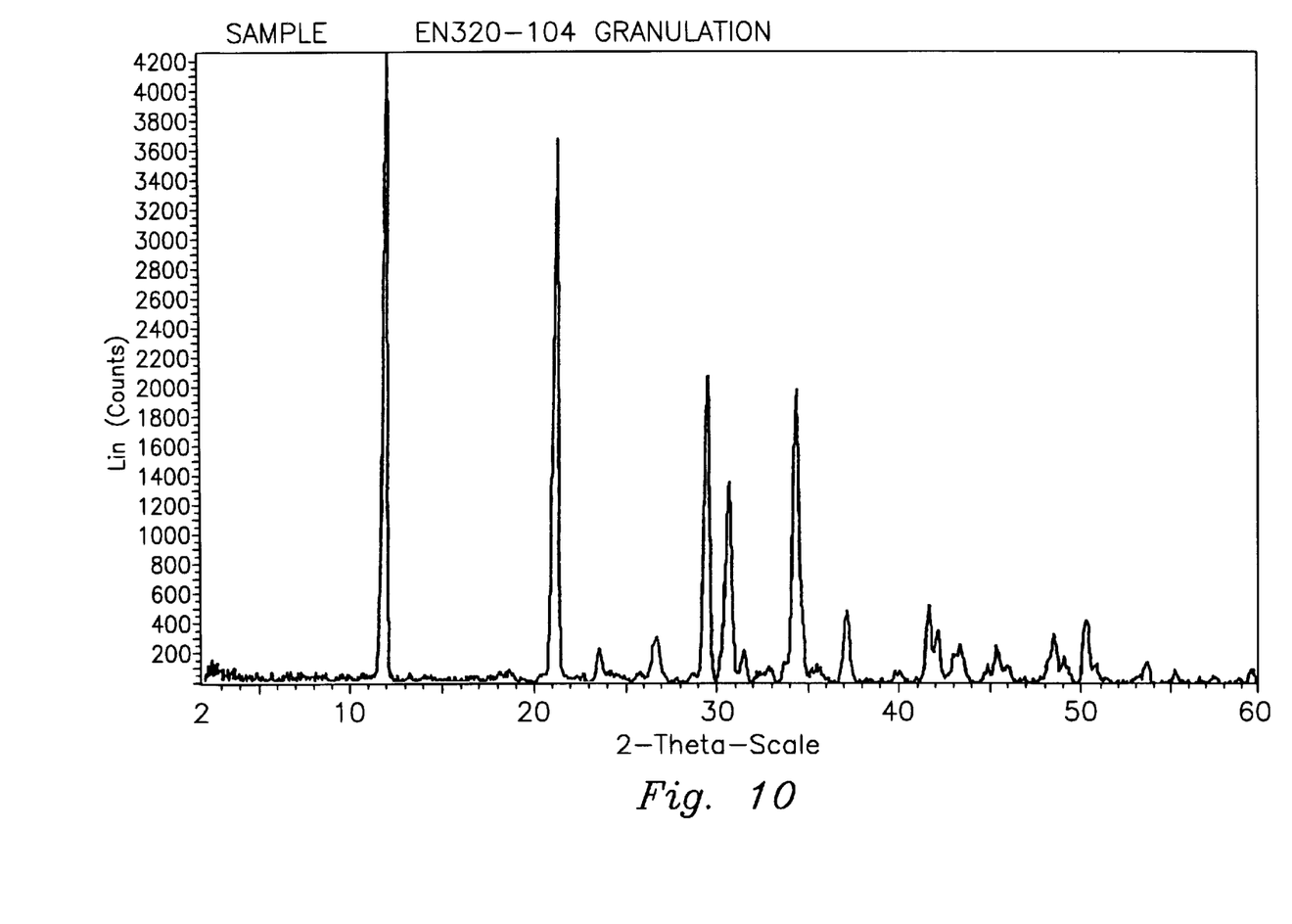
FIG. 10 is an x-ray powder defraction analysis of Sample No. EN320-104.

To a 250 mL flask (equipped with a magnetic stir bar) was added PVP 29/32K (11.11 g), paroxetine hydrochloride anhydrous isopropyl alcohol solvate (22.21 g) and purified water (279.1 g). The contents of the flask were stirred and heated to a temperature of approximately 60° C. with a stirring hotplate to obtain a clear solution. The hot solution was spray dried onto dibasic calcium phosphate dihydrate (100.0 g) using a bench top fluid bed dryer. FTIR (FIG. 9) analysis of the solid, free-flowing powder, identified as EN320-104, was consistent with a mixture of dibasic calcium phosphate dihydrate, PVP and paroxetine hydrochloride. X-ray powder diffraction (FIG. 10) analysis of powder was wholly consistent with a mixture of dibasic calcium phosphate dihydrate and PVP, indicating absence of crystalline paroxetine and that the paroxetine was present in amorphous form only. The FTIR data was collected using a Nicolet 510P FT-IR spectrometer. A Nujol mull was prepared for the sample and analyzed on a KBr plate. The x-ray powder patterns were obtained using a Bruker Analytical GADDS system. The diffractometer was equipped with a point x-ray source and a 2-dimensional area detector. The radiation was CuK (alpha, 50 kV, 40 mA). The data were collected at room temperature from 2 to 60 degrees 2-theta; the detector range was 30 degrees; the number of frames was 3; the data collection time was 600 sec/frame. The sample was mounted for reflection mode data collection by pressing the sample into a small round sample holder.

Example 6
A 21 MG PAROXETINE HCL TABLET

A 21 mg tablet was prepared using a solid dispersion prepared according to Example 3, and identified as EN 320-006, had the following ingredients and amounts:

| Ingredient | mg/tablet | gm/batch |
|---|---|---|
| Paroxetine HCl* | 21.00 | 3.51 |
| PVP 29/32K* | 42.00 | 7.02 |
| Dibasic calcium phosphate dihydrate* | 300.11 | 50.17 |
| Sodium Starch Glycolate | 24.00 | 4.00 |
| Magnesium Stearate | 9.00 | 1.50 |
| Total | 396.11 mg | 66.2 gm |

Figure 11:
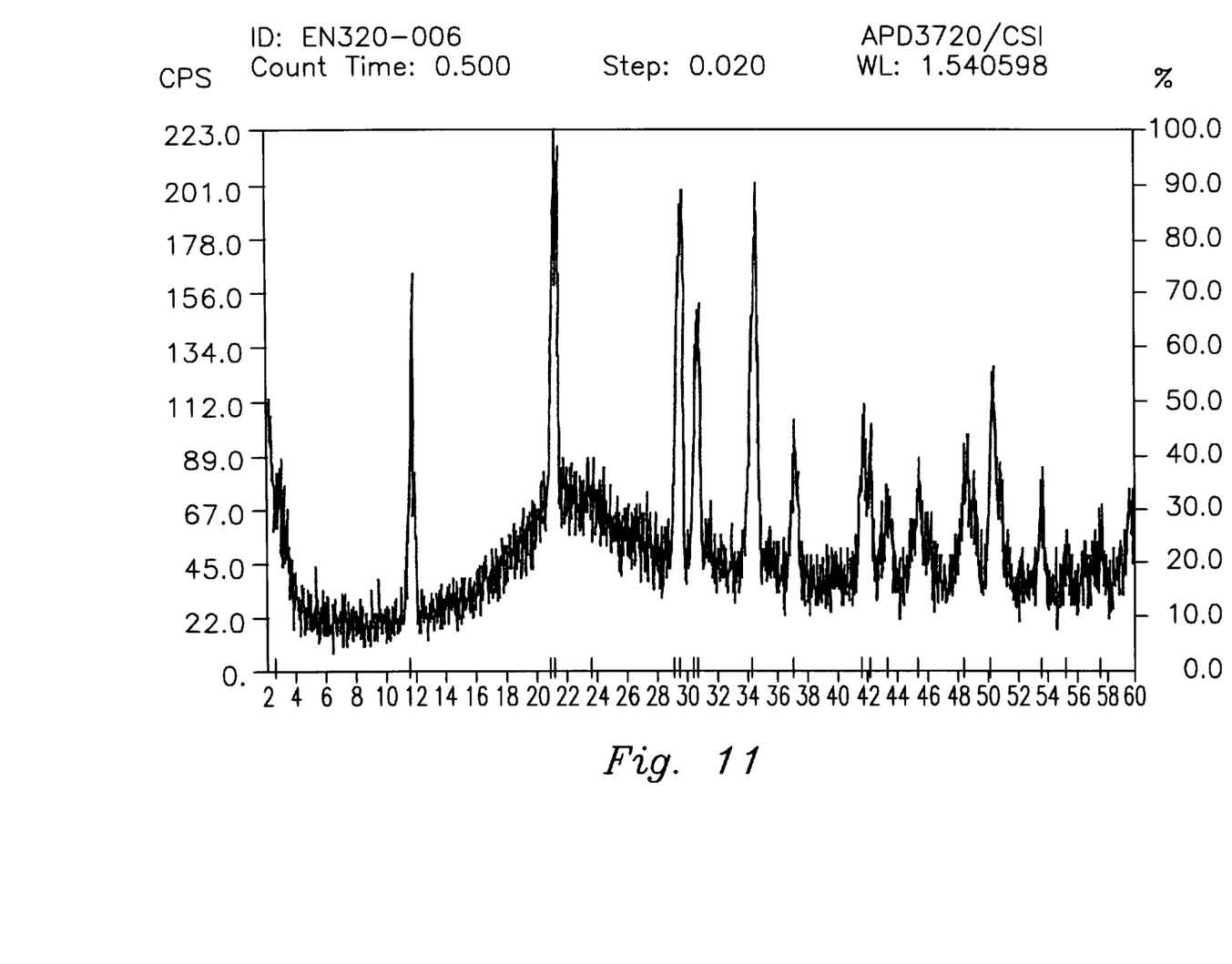
FIG. 11 is an x-ray powder defraction analysis of ground tablets (Sample No. EN320-006) with coating removed after 14 weeks of storage at 40° C./75% relative humidity.

*Theoretical quantities for Paroxetine HCl, PVP and dibasic calcium phosphate dihydrate The tablet was prepared according to the following procedure: Mill the paroxetine HCl/PVP/dibasic calcium phosphate dihydrate by passing through a 20 mesh screen. Blend the milled material with the sodium starch glycolate and magnesium stearate. Compress tablets to a weight of 396.11 mg. The tablets were then coated with a commercially available color film coating. X-ray powder diffraction (FIG. 11) analysis was preformed on ground tablets (lot EN320-006) with coating removed after 14 weeks of storage at 40° C./75% relative humidity. The diffractogram was wholly consistent with a mixture of dibasic calcium phosphate dihydrate, PVP, sodium starch glycolate and magnesium stearate indicating absence of crystalline paroxetine and that the paroxetine was present in amorphous form only. The x-ray powder: patterns were obtained using a Philips model 3720 automated powder diffractometer. The diffractometer was equipped with a varaible slit (theta-compensating slit), a scintillation counter, and a graphite monochromater. The radiation was CuK (alpha, 40 kV, 30 mA). The data were collected at room temperature from 2 to 60 degrees 2-theta; the step size was 0.02 degrees; the count time was 0.5 sec/step. The sample was prepared on a glass specimen holder as a thin layer of powdered material in a dry neat state.

Example 7
A 22.21 MG PAROXETINE HCL TABLET USING A SOLID DISPERSION AS DESCRIBED IN EXAMPLE 4

A 22.21 mg paroxetine HCl tablet was prepared using a solid dispersion as described in Example 4 (EN320-073).

| Ingredient | mg/tablet | gm/batch |
|---|---|---|
| Paroxetine HCl* | 22.21 | 20.11 |
| PVP 29/32K* | 22.24 | 20.14 |
| Dibasic calcium phosphate dihydrate* | 187.44 | 169.75 |
| Dibasic calcium phosphate dihydrate | 29.15 | 26.40 |
| Sodium Starch Glycolate | 24.00 | 21.74 |
| Magnesium Stearate | 15.00 | 13.59 |
| Total | 300.04 mg | 271.73 gm |

*Theoretical quantities for Paroxetine HCl, PVP and dibasic calcium phosphate dihydrate product as described in Example 4.

Figure 12:
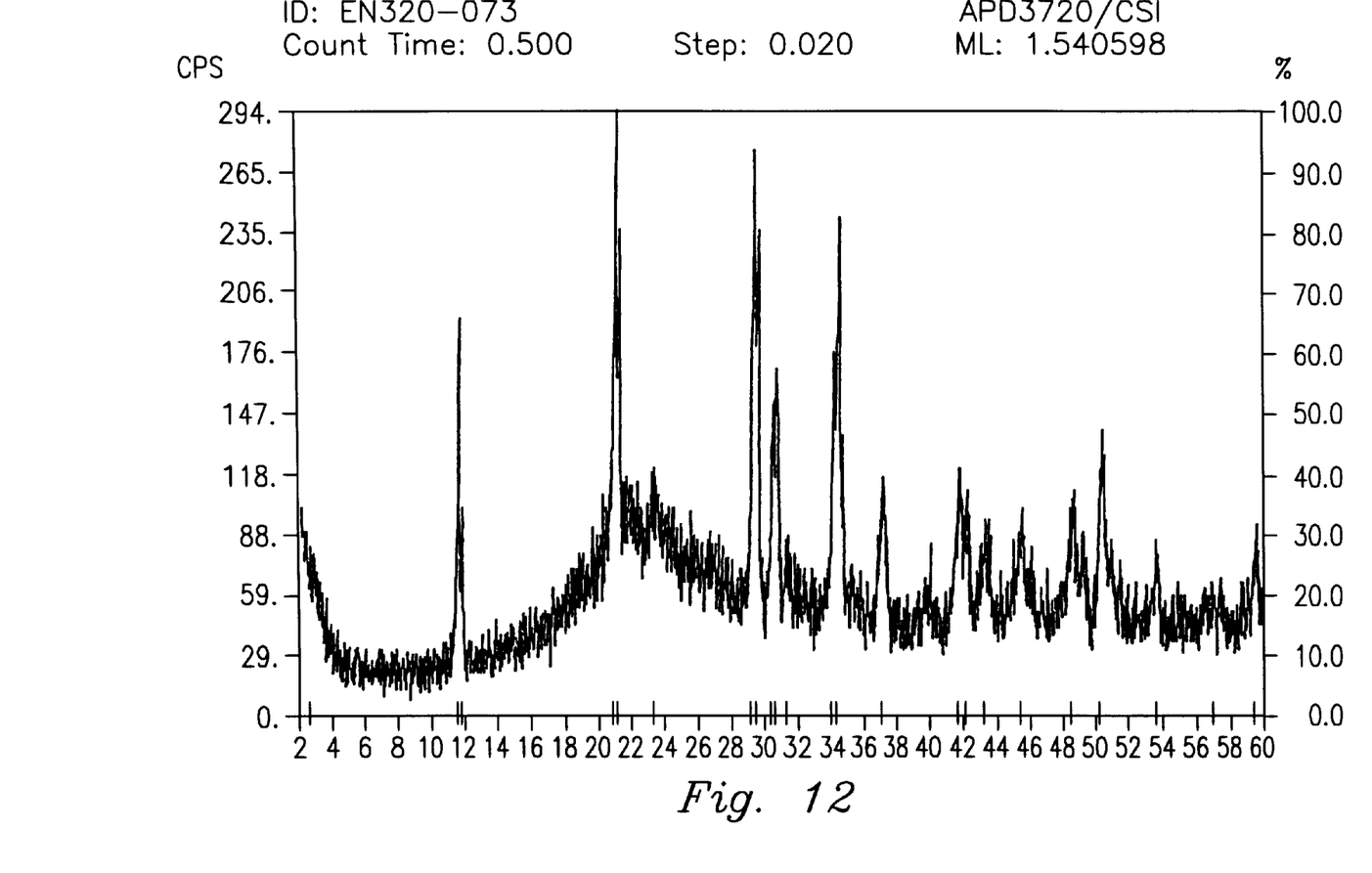
FIG. 12 is an x-ray powder defraction analysis on ground tablets (Sample No. EN320-073) with coating removed after 3 weeks of storage at 40° C./75% relative humidity.

The tablets were prepared by the following procedure: Mill the paroxetine HCl/PVP/dibasic calcium phosphate dihydrate by passing through a 20 mesh screen. Blend the milled material with the sodium starch glycolate and magnesium stearate. Compress tablets to a weight of 300 mg. The tablets were then coated with a commercially available color film coating. X-ray powder diffraction (FIG. 12) analysis was preformed on ground tablets with coating removed after 3 weeks of storage at 40° C./75% relative humidity. The diffractogram was wholly consistent with a mixture of dibasic calcium phosphate dihydrate, PVP, sodium starch glycolate and magnesium stearate indicating absence of crystalline paroxetine and that the paroxetine was present in amorphous form only. The x-ray powder patterns were obtained using a Philips model 3720 automated powder diffractometer. The diffractometer was equipped with a variable slit (theta-compensating slit), a scintillation counter, and a graphite monochromater. The radiation was CuK (alpha, 40 kV, 30 mA). The data were collected at room temperature from 2 to 60 degrees 2-theta; the step size was 0.02 degrees; the count time was 0.5 sec/step. The sample was prepared on a glass specimen holder as a thin layer of powdered material in a dry neat state.

While the invention has been described above in great detail, various modifications, alternative embodiments, and improvements to the invention disclosed herein should become readily apparent to those skilled in this art, without departing from the spirit and scope of the invention.

What is claimed is:

1. A process for preparing solid, amorphous paroxetine comprising:
   (A) mixing paroxetine free base or a pharmaceutically acceptable paroxetine salt with water and pharmaceutically acceptable polymer; and
   (B) drying to form a composition comprising solid amorphous paroxetine and polymer wherein said polymer is at least partially water soluble.

2. Process according to claim 1 wherein said solid amorphous paroxetine is free of calcium polycarbophil.

3. Process according to claim 1 wherein said polymer is water soluble.

4. Process according to claim 1 further including forming a solution of said paroxetine salt and said polymer.

5. Process according to claim 1 wherein said polymer is water soluble and a solution in water of said paroxetine or paroxetine salt is formed upon or after said mixing.

6. Process according to claim 1 wherein said solid amorphous paroxetine and polymer is immediate release.

7. Process according to claim 1 wherein said polymer is not of a character which controls or delays the release of said paroxetine from a solid tablet formulation.

8. Process according to claim 1 wherein said solid amorphous paroxetine is free of any water-swellable, insoluble, fibrous cross-linked carboxy-functional polymer.

9. Process according to claim 1 wherein said paroxetine is added as a pharmaceutically acceptable salt.

10. Process according to claim 9 wherein said acid corresponding to a pharmaceutically acceptable salt of paroxetine is a hydrochloride salt.

11. Process according to claim 1 wherein said paroxetine is added in free base form and the process further comprises adding an acid corresponding to a pharmaceutically acceptable salt of paroxetine.

12. Process according to claim 11 wherein the molar ratio of said paroxetine to said acid is about 1:1 to 1:1.8.

13. Process according to claim 12 wherein the molar ratio of paroxetine to said acid is about 1:1 to about 1:1.1.

14. Process according to claim 11 wherein said paroxetine free base is obtained by basifying paroxetine acid salt.

15. Process according to claim 11 wherein the acid is HCl, the molar ratio of paroxetine to HCl is about 1:1 to 1:1.8, said polymer is selected from the group consisting of polyvinylpyrrolidone, hydroxypropylmethyl cellulose, hydroxypropyl cellulose, methyl cellulose, block co-polymers of ethylene oxide and propylene oxide, and polyethylene glycol, and said drying comprises spray drying to form a solid which is mixed with excipients and tabletized.

16. Process according to claim 1 wherein said mixing is conducted at elevated temperature.

17. Process according to claim 16 wherein said elevated temperature is about 25 to 100° C.

18. Process according to claim 17 wherein said elevated temperature is about 60° C.

19. Process according to claim 1 wherein said polymer is selected from the group consisting of polyvinylpyrrolidone, hydroxypropylmethyl cellulose, hydroxypropyl cellulose, methyl cellulose, block co-polymers of ethylene oxide and propylene oxide, and polyethylene glycol.

20. Process according to claim 19 wherein said polymer is polyvinylpyrrolidone.

21. Process according to claim 20 wherein said polyvinylpyrrolidone has an average molecular weight of about 2,500 to about 3,000,000.

22. Process according to claim 1 wherein said drying comprises spray drying onto a substrate.

23. Process according to claim 22 wherein said substrate is calcium phosphate.

24. Process according to claim 1 wherein the resultant dried, amorphous solid is mixed with pharmaceutically acceptable excipient(s) and tabletized.

25. Process according to claim 24 wherein said pharmaceutically acceptable excipient is selected from the group consisting of calcium carbonate, calcium phosphate, calcium sulfate, cellulose, cellulose derivatives, croscarmallose sodium, cospovidone, dextrates, dextrin, dextrose, fructose, guar gum, lactose, maltodextrin, mannitol, povidone, starch, sorbitol, sucrose, xylitol and mixtures thereof.

26. Process according to claim 1 wherein the weight ratio of polymer to paroxetine is about 0.4:1 to 20:1.

27. A pharmaceutical composition comprising paroxetine salt in amorphous form, and polymer, prepared by a process according to claim 1.

28. Pharmaceutical composition according to claim 27 wherein said salt is the hydrochloride and said polymer is selected from the group consisting of polyvinylpyrrolidone, hydroxypropylmethyl cellulose, hydroxypropyl cellulose, methyl cellulose, block co-polymers of ethylene oxide and propylene oxide, and polyethylene glycol.

29. A process of treating a warm-blooded animal comprising administering to said animal a composition according to claim 27.

30. Process according to claim 1 wherein the pharmaceutically acceptable polymer is water soluble.

31. Process according to claim 1 wherein the process further comprises forming a clear solution.

32. Process according to claim 31 wherein said drying comprises spray drying said clear solution onto pharmaceutically acceptable excipient to form a solid comprising amorphous paroxetine and crystalline material.

33. Process according to claim 31 wherein said mixing is conducted at elevated temperature, wherein said polymer is polyvinylpyrrolidone, said drying comprises spray drying said clear solution onto amorphous or crystalline substrate, and the resultant dried, amorphous paroxetine on substrate is mixed with excipients and tabletized.

* * * * *